US008993348B2

(12) United States Patent
Wheeler et al.

(10) Patent No.: US 8,993,348 B2
(45) Date of Patent: *Mar. 31, 2015

(54) EXCHANGEABLE CARRIERS PRE-LOADED WITH REAGENT DEPOTS FOR DIGITAL MICROFLUIDICS

(75) Inventors: Aaron R. Wheeler, Toronto (CA); Irena Barbulovic-Nad, Toronto (CA); Hao Yang, Toronto (CA); Mohamed Abdelgawad, Toronto (CA)

(73) Assignee: The Governing Council of the University of Toronto, Toronto, ON (CA)

(*) Notice: Subject to any disclaimer, the term of this patent is extended or adjusted under 35 U.S.C. 154(b) by 654 days.

This patent is subject to a terminal disclaimer.

(21) Appl. No.: 13/122,311

(22) PCT Filed: Sep. 30, 2009

(86) PCT No.: PCT/EP2009/062657

§ 371 (c)(1), (2), (4) Date: Jun. 20, 2011

(87) PCT Pub. No.: WO2010/037763

PCT Pub. Date: Apr. 8, 2010

(65) Prior Publication Data

US 2011/0240471 A1 Oct. 6, 2011

Related U.S. Application Data

(63) Continuation-in-part of application No. 12/285,326, filed on Oct. 1, 2008, now Pat. No. 8,187,864.

(51) Int. Cl.
*G01N 33/543* (2006.01)
*B01L 3/00* (2006.01)

(52) U.S. Cl.
CPC ..... *B01L 3/502784* (2013.01); *B01L 2200/027* (2013.01); *B01L 2200/141* (2013.01);

(Continued)

(58) Field of Classification Search
CPC ........................ B01L 3/502784
USPC ............ 436/518; 435/287.1, 287.2, 287.6
See application file for complete search history.

(56) References Cited

U.S. PATENT DOCUMENTS 4,569,575 A 2/1986 Le Pesant et al.
4,636,785 A 1/1987 Le Pesant (Continued)

FOREIGN PATENT DOCUMENTS

WO 2007120241 A2 10/2007
WO 2007136386 A1 11/2007
WO 2008/051310 5/2008

OTHER PUBLICATIONS

Shih-Kang Fan. "Cross-scale electric manipulations of cells and droplets by frequency-modulated dielectrophoresis and electrowetting" The Royal Society of Chemistry (2008), Lab Chip vol. 8, pp. 1326-1331.

(Continued)

*Primary Examiner* — Melanie Y Brown
(74) *Attorney, Agent, or Firm* — Lynn C. Schumacher; Stephen W. Leonard; Hill & Schumacher

(57) ABSTRACT

The present invention provides exchangeable, reagent pre-loaded carriers (10), preferably in the form of plastic sheets, which can be temporarily applied to an electrode array (16) on a digital microfluidic (DMF) device (14). The carrier (10) facilitates virtually un-limited re-use of the DMF devices (14) avoiding cross-contamination on the electrode array (16) itself, as well as enabling rapid exchange of pre-loaded reagents (12) while bridging the world-to-chip interface of DMF devices (14). The present invention allows for the transformation of DMF into a versatile platform for lab-on-a-chip applications.

34 Claims, 6 Drawing Sheets

(52) U.S. Cl.
CPC ........ *B01L2200/16* (2013.01); *B01L 2300/046* (2013.01); *B01L 2300/0867* (2013.01); *B01L 2300/161* (2013.01); *B01L 2400/0427* (2013.01)
USPC ..................... 436/518; 435/287.1; 435/287.2; 435/287.6

(56) References Cited

U.S. PATENT DOCUMENTS

| | | | | |
|---|---|---|---|---|
| 4,818,052 | A | 4/1989 | Le Pesant et al. | |
| 5,486,337 | A | 1/1996 | Ohkawa | |
| 6,352,838 | B1 | 3/2002 | Krulevitch et al. | |
| 6,565,727 | B1 | 5/2003 | Shenderov | |
| 6,773,566 | B2 | 8/2004 | Shenderov | |
| 6,911,132 | B2 | 6/2005 | Pamula et al. | |
| 6,989,234 | B2 | 1/2006 | Kolar et al. | |
| 7,147,763 | B2 | 12/2006 | Elrod et al. | |
| 7,163,612 | B2 | 1/2007 | Sterling et al. | |
| 7,214,302 | B1 | 5/2007 | Reihs et al. | |
| 7,255,780 | B2 | 8/2007 | Shendervo | |
| 7,328,979 | B2 | 2/2008 | Decre et al. | |
| 7,329,545 | B2 | 2/2008 | Pamula et al. | |
| 2002/0043463 | A1 | 4/2002 | Shenderov | |
| 2002/0144905 | A1* | 10/2002 | Schmidt | 204/403.01 |
| 2003/0003223 | A1 | 1/2003 | Morse et al. | |
| 2003/0164295 | A1* | 9/2003 | Sterling | 204/450 |
| 2005/0115836 | A1 | 6/2005 | Reihs | |
| 2005/0148091 | A1 | 7/2005 | Kitaguchi et al. | |
| 2005/0191759 | A1 | 9/2005 | Pedersen-Bjergaard et al. | |
| 2007/0023292 | A1 | 2/2007 | Kim et al. | |
| 2007/0148763 | A1 | 6/2007 | Huh et al. | |
| 2007/0242111 | A1 | 10/2007 | Pamula et al. | |
| 2008/0044914 | A1 | 2/2008 | Pamula et al. | |
| 2008/0156983 | A1 | 7/2008 | Fourrier et al. | |
| 2008/0185339 | A1 | 8/2008 | Delapierre et al. | |
| 2009/0203063 | A1 | 8/2009 | Wheeler et al. | |
| 2010/0081578 | A1 | 4/2010 | Wheeler et al. | |
| 2010/0282609 | A1 | 11/2010 | Pollack et al. | |
| 2010/0311599 | A1 | 12/2010 | Wheeler et al. | |

OTHER PUBLICATIONS

Ting-Hsuan Chen. "Selective Wettability Assisted Nanoliter Sample Generation Via Eiectrowetting-Based Transportation " Proceedings of the Fifth International Conference on Nanochannels, Microchannels and Minichannels. (ICNMM) (Jun. 18-20, 2007).

Hongmei Yu. "A plate reader-compatible microchannel array for cell biology assays," The Royal Society of Chemistry (2007) Lab Chip vol. 7, pp. 388-391.

Marc A. Unger. " Monolithic Microtabricated Valves and Pumps by Multilayer Soft Lithography;" Science (2000) vol. 288.

A.S. Verkma "Drug Discovery in Academia," Am J Physiol Cell Physiol (2004) vol. 286, pp. 465-474.

Jamil El-Ali. "Cells on chips" Nature (2006) Insight Review, vol. 442.

Darren R. Link. "Electric Control of Droplets in Microfluidic Devices," Communications, Angew Chem. Int (2006) vol. 45 pp. 2556-2560.

Wheeler Aaron A. "Electrowetting-Based Microfluidics for Analysis of Peptides and Proteins by Metrix-Assisted Laser Desorption/Ionization Mass Spectrometry." (Aug. 2004) Anal Chem. vol. 76, No. 16.

Eun Zoo Lee, "Removal of bovine serum albumin using solid-phase extraction with in-situ polymerized stationary phase in a microfluidic device," ScienceDirect, Journal of Chromatography A. (2008) vol. 1187, pp. 11-17.

Hsih Yin Tan, "A lab-on-a-chip for detection of nerve agent sarin in blood," The Royal Society of Chemistry (2008), Lab Chip vol. 8, pp. 885-891.

Hyejin Moon. An integrated digital microfluidic chip for multiplexed proteornic sample preparation and analysis by MALDI-MS, The Royal Society of Chemistry (2006), Lab Chip vol. 6, pp. 1213-1219.

Mais J. Jebrail "Digital Microfluidic Method for Protein Extraction by Precipitation," Anal. Chem. 2009 vol. 81, No. 1.

Debalina Chatterjee. "Droplet-based microfluidics with nonaqueous solvents and solutions," The Royal Society of Chemistry (2006), Lab Chip vol. 6, pp. 199-206.

Lebrasseur, et al., "Two-dimensional electrostatic actuation of droplets using a single electrode panel and development of disposable plastic film card", Sensors and Actuators A, Apr. 19, 2007, pp. 358-366, vol. 136, No. 1.

Adbelgawad et al., "Low-cost rapid-prototyping of digital microfluidics devices", Microfluid Nanofluid (2008) vol. 4 pp. 349-355, Springer-Verlag (2007).

Chuang et al., "Direct Handwriting Manipulation of Droplets by Self-Aligned Mirror-EWOD Across a Dielectric Sheet", Institute of Nanotechnology National Chiao Tung University Hsinchu Taiwan, MEMS (2006) pp. 22-26, Istanbul-Turkey (2006).

U.S. Appl. No. 60/980,622, filed Oct. 17, 2007 from which PCTUS2008/079812 (filed Oct. 14, 2008) claims priority.

* cited by examiner

* = Predicted Peptide

EXCHANGEABLE CARRIERS PRE-LOADED WITH REAGENT DEPOTS FOR DIGITAL MICROFLUIDICS

This patent application is a National Phase application claiming the benefit of PCT/EP2009/062657 filed on Sep. 30, 2009, in English, entitled EXCHANGEABLE CARRIERS PRE-LOADED WITH REAGENT DEPOTS FOR DIGITAL MICROFLUIDICS; which further claims priority of the U.S. patent application Ser. No. 12/285,326 filed on Oct. 1, 2008 now U.S. Pat. No. 8,187,864, the whole content of which is incorporated herein by explicit reference for all intents and purposes.

FIELD OF THE INVENTION

The present invention relates to exchangeable, reagent pre-loaded carriers for digital microfluidics, and more particularly the present invention relates to removable plastic sheets on which reagents are strategically located in pre-selected positions as exchangeable carriers for digital microfluidic (DMF) devices.

BACKGROUND TO THE INVENTION

Microfluidics deals with precise control and manipulation of fluids that are geometrically constrained to small, typically microliter, volumes. Because of the rapid kinetics and the potential for automation, microfluidics can potentially transform routine bioassays into rapid and reliable tests for use outside of the laboratory. Recently, a new paradigm for miniaturized bioassays has been emerged called "digital" (or droplet based) microfluidics. Digital microfluidics (DMF) relies on manipulating discrete droplet of fluids across a surface of patterned electrodes, see e.g. U.S. Pat. No. 7,147,763; U.S. Pat. No. 4,636,785; U.S. Pat. No. 5,486,337; U.S. Pat. No. 6,911,132; U.S. Pat. No. 6,565,727; U.S. Pat. No. 7,255,780; JP 10-267801; or Lee et al. 2002 "Electrowetting and electrowetting-on-dielectric for microscale liquid handling" *Sensors & Actuators* 95: 259-268; Pollack et al. 2000 "Electrowetting-based actuation of liquid droplets for microfluidic applications" *Applied Physics Letters* 77: 1725-1726; and Washizu, M. 1998 "Electrostatic actuation of liquid droplets for microreactor applications" *IEEE Transactions on Industry Applications* 34: 732-737. This technique is analogous to sample processing in test tubes, and is well suited for array-based bioassays in which one can perform various biochemical reactions by merging and mixing those droplets. More importantly, the array based geometry of DMF seems to be a natural fit for large, parallel scaled, multiplexed analyses. In fact, the power of this new technique has been demonstrated in a wide variety of applications including cell-based assays, enzyme assays, protein profiling, and the polymerase chain reaction.

Unfortunately, there are two critical limitations on the scope of applications compatible with DMF—biofouling and interfacing. The former limitation, biofouling, is a pernicious one in all micro-scale analyses—a negative side-effect of high surface area to volume ratios is the increased rate of adsorption of analytes from solution onto solid surfaces. We and others have developed strategies to limit the extent of biofouling in digital microfluidics, but the problem persists as a road-block, preventing wide adoption of the technique.

The second limitation for DMF (and for all microfluidic systems) is the "world-to-chip" interface—it is notoriously difficult to deliver reagents and samples to such systems without compromising the oft-hyped advantages of rapid analyses and reduced reagent consumption. A solution to this problem for microchannel-based methods is the use of pre-loaded reagents. Such methods typically comprise two steps:

(1) reagents are stored in microchannels (or in replaceable cartridges), and
(2) at a later time, the reagents are rapidly accessed to carry out the desired assay/experiment.

Two strategies have emerged for microchannel systems—in the first, reagents are stored as solutions in droplets isolated from each other by plugs of air (see Linder et al. 2005 "Reagent-loaded cartridges for valveless and automated fluid delivery in microfluidic devices" *Analytical Chemistry* 77: 64-71) or an immiscible fluid (see Hatakeyama et al. 2006 "Microgram-scale testing of reaction conditions in solution using nanoliter plugs in microfluidics with detection by MALDI-MS" *Journal of the American Chemical Society* 128: 2518-2519 and Zheng et al. 2005 "A microfluidic approach for screening submicroliter volumes against multiple reagents by using preformed arrays of nanoliter plugs in a three-phase liquid/liquid/gas flow" *Angewandte Chemie—International Edition* 44: 2520-2523) until use. In a second, reagents are stored in solid phase in channels, and are then reconstituted in solution when the assay is performed (Furuberg et al. 2007 "The micro active project: Automatic detection of disease-related molecular cell activity" *Proceedings of SPIE-Int. Soc. Opt. Eng.*; Garcia et al. 2004 "Controlled microfluidic reconstitution of functional protein from an anhydrous storage depot" *Lab on a Chip* 4: 78-82; and Zimmermann et al. 2008 "Autonomous capillary system for one-step immunoassays" *Biomedical Microdevices*). Pre-loaded reagents in microfluidic devices is a strategy that will be useful for a wide range of applications. Until now, however, there has been no analogous technique for digital microfluidics.

In response to the twin challenges of non-specific adsorption and world-to-chip interfacing in digital microfluidics, we have developed a new strategy relying on removable polymer coverings (see Abdelgawad and Wheeler 2008 "Low-cost, rapid-prototyping of digital microfluidics devices" *Microfluidics and Nanofluidics* 4: 349-355; Chuang and Fan 2006 "Direct handwriting manipulation of droplets by self-aligned mirror-EWOD across a dielectric sheet" *Proceedings of Mems: 19th IEEE International Conference on Micro Electro Mechanical Systems, Technical Digest:* 538-541; and Lebrasseur et al. 2007 "Two-dimensional electrostatic actuation of droplets using a single electrode panel and development of disposable plastic film card" *Sensors and Actuators a-Physical* 136: 358-366). After each experiment, a thin film is replaced, but the central infrastructure of the device is reused. This effectively prevents cross-contamination between repeated analyses, and perhaps more importantly, serves as a useful medium for reagent introduction onto DMF devices.

SUMMARY AND OBJECTIVES OF THE INVENTION

To demonstrate this principle of using a single electrode panel and of disposable plastic coverings, we pre-loaded dried spots of enzymes to the plastic coverings for subsequent use in proteolytic digestion assays. The loaded reagents were found to be active after >1 month of storage in a freezer. As the first technology of its kind, we propose that this innovation may represent an important step forward for digital microfluidics, making it an attractive fluid-handling platform for a wide range of applications. Even using a two-plate design (with or without double electrode panel) turned out to be applicable to reagent pre-loaded carriers according to the present invention.

The present invention provides removable, disposable carriers, e.g. plastic sheets which are be pre-loaded with reagents. The new method involves manipulating reagent and sample droplets on DMF devices that have been attached with pre-loaded carriers. When an assay is complete, the sheet can be removed, analyzed, if desired, and the original device can be reused by reattaching a fresh pre-loaded sheet to start another assay.

These removable, disposable plastic films, pre-loaded with reagents, facilitate rapid, batch scale assays using DMF devices with no problems of cross-contamination between assays. In addition, the reagent cartridge devices and method disclosed herein facilitate the use of reagent storage depots. For example, the inventors have fabricated sheets with pre-loaded dried spots containing enzymes commonly used in proteomic assays, such as trypsin or α-chymotrypsin. After digestion of the model substrate ubiquitin, the product-containing sheets were evaluated by matrix assisted laser desorption/ionization mass spectrometry (MALDI-MS). The present invention very advantageously elevates DMF to compatibility with diverse applications ranging from laboratory analyses to point-of-care diagnostics.

Thus, an embodiment of the present invention includes a carrier (preferably in the form of a sheet or film) that is pre-loaded with reagents for use with a digital microfluidic device, the digital microfluidic device including an electrode array, said electrode array including an array of discrete electrodes, the digital microfluidic device including an electrode controller, the pre-loaded carrier comprising:

an electrically insulating sheet having a back surface and a front hydrophobic surface, said electrically insulating sheet being removably attachable to said electrode array of the digital microfluidic device with said back surface being adhered to a surface of said electrode array, said electrically insulating sheet covering said discrete electrodes for insulating the discrete electrodes from each other and from liquid droplets on the front hydrophobic surface, wherein said electrically insulating sheet has one or more reagent depots located in one or more pre-selected positions on the front hydrophobic surface of the electrically insulating sheet;

wherein in operation the electrode controller being capable of selectively actuating and de-actuating said discrete electrodes for translating liquid droplets over the front hydrophobic surface of the electrically insulating sheet; and wherein said one or more pre-selected positions on said front working surface of said electrically insulating sheet are positioned to be accessible to droplets actuated over the front hydrophobic surface of the electrically insulating sheet.

In another embodiment of the present invention there is provided a digital microfluidic device, comprising:

a first substrate having mounted on a surface thereof an electrode array, said electrode array including an array of discrete electrodes, the digital microfluidic device including an electrode controller capable of selectively actuating and de-actuating said discrete electrodes;

an electrically insulating sheet having a back surface and a front hydrophobic surface, said electrically insulating sheet being removably attached to said electrode array of the digital microfluidic device (preferably with said back surface being adhered to said array of discrete electrodes), said electrically insulating sheet electrically insulating said discrete electrodes from each other in said electrode array and from liquid droplets on the front hydrophobic surface, said electrically insulating sheet having one or more reagent depots located in one or more pre-selected positions on the front hydrophobic surface of the electrically insulating sheet, said one or more pre-selected positions on said front hydrophobic surface being positioned to be accessible to the liquid droplets actuated over the front hydrophobic surface of the electrically insulating sheet;

wherein liquid droplets are translatable across said front hydrophobic surface to said one or more reagent depots by selectively actuating and de-actuating said discrete electrodes under control of said electrode controller.

In an embodiment of the apparatus there may be included a second substrate having a front surface which is optionally a hydrophobic surface, wherein the second substrate is in a spaced relationship to the first substrate thus defining a space between the first and second substrates capable of containing droplets between the front surface of the second substrate and the front hydrophobic surface of the electrically insulating sheet on said electrode array on said the substrate. An embodiment of the device may include an electrode array on the second substrate, covered by a dielectric sheet. In this case the electrode array on the first substrate may be optional and hence may be omitted. There may also be insulating sheets pre-loaded with reagent depots on one or both of the substrates.

The present invention also provides a digital microfluidic method, comprising the steps of:

preparing a digital microfluidic device having an electrode array including an array of discrete electrodes, the digital microfluidic device including an electrode controller connected to said array of discrete electrodes for applying a selected pattern of voltages to said discrete electrodes for selectively actuating and de-actuating said discrete electrodes in order to move liquid sample drops across said electrode array in a desired pathway over said discrete electrodes;

providing a removably attachable electrically insulating sheet having a back surface and a front working surface;

removably attaching said electrically insulating sheet to said electrode array of the digital microfluidic device (preferably with said back surface being adhered thereto), said electrically insulating sheet having hydrophobic front surface and one or more reagent depots located in one or more pre-selected positions on the front working surface of the electrically insulating sheet, said one or more pre-selected positions on said front working surface of said electrically insulating sheet are positioned to be accessible to droplets actuated over the front working surface of the electrically insulating sheet;

conducting an assay by directing one or more sample droplets over said front working surface to said one or more reagent depots whereby the one or more sample droplets is delivered to said one or more reagent depots which is reconstituted by the one or more sample droplets and mixed with at least one selected reagent contained in the one or more reagent depots;

isolating any (or at least one) resulting reaction product formed between said mixed sample droplet and said at least one selected reagent in each (or at least one) of said one or more reagent depots; and optionally removing said removably attachable electrically insulating sheet from the surface of the electrode array of the digital microfluidic device and preparing the digital microfluidic device for a new assay.

A further understanding of the functional and advantageous aspects of the invention can be realized by reference to the following detailed description and drawings. Additional elements of the present invention and additional preferred embodiments arise from the dependent claims.

BRIEF DESCRIPTION OF THE DRAWINGS

Exemplary embodiments of the present invention are described in greater detail with reference to the accompanying drawings that shall not limit the scope of the present invention. There is shown in.

Figure 3:
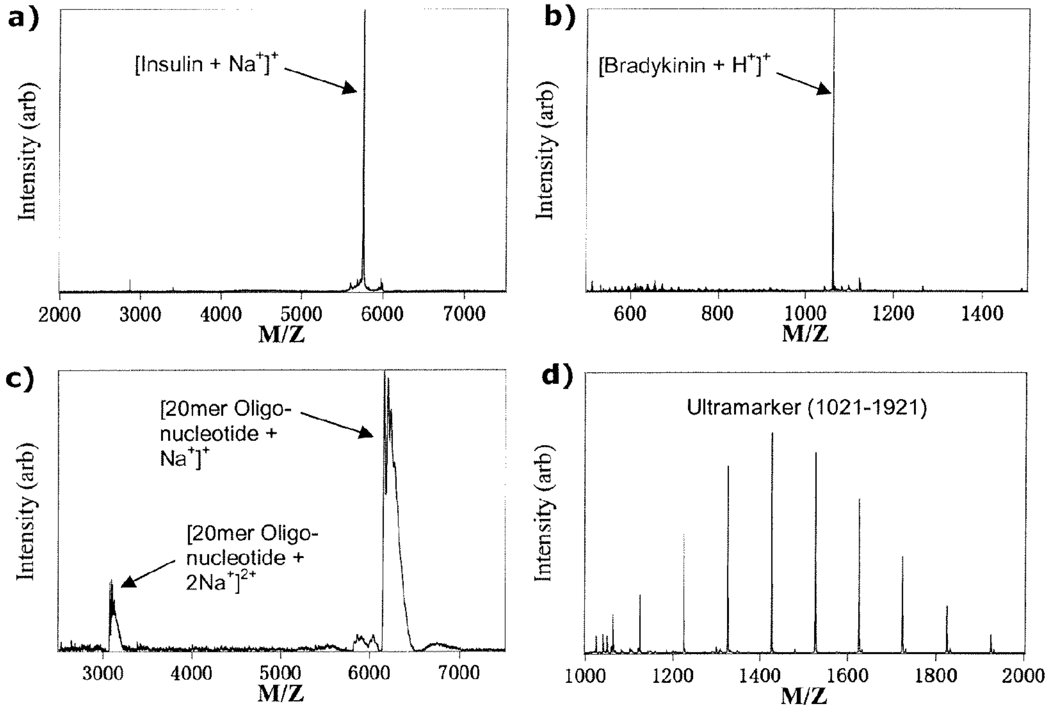
Figure 4:
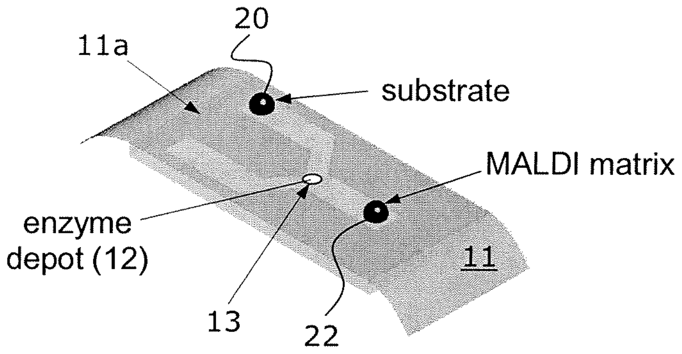
Figure 4:
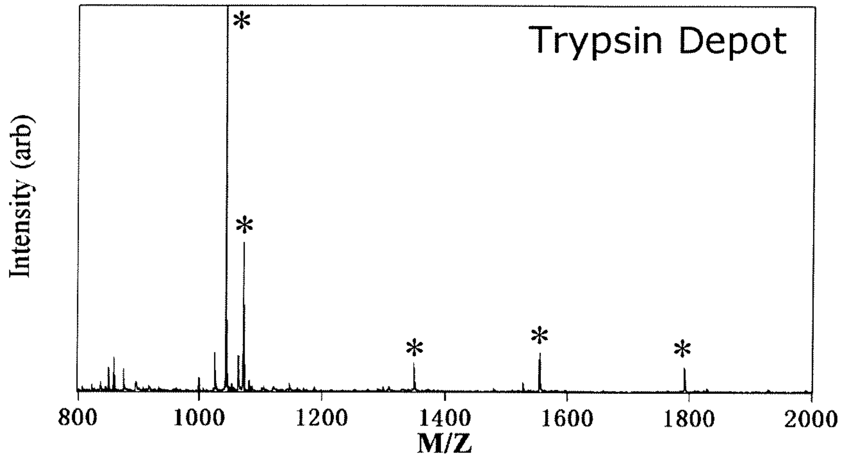
Figure 4:
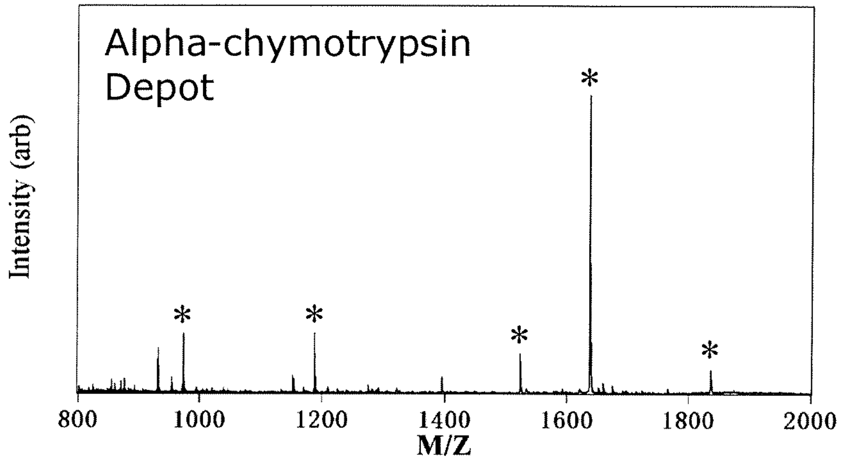
Figure 5:
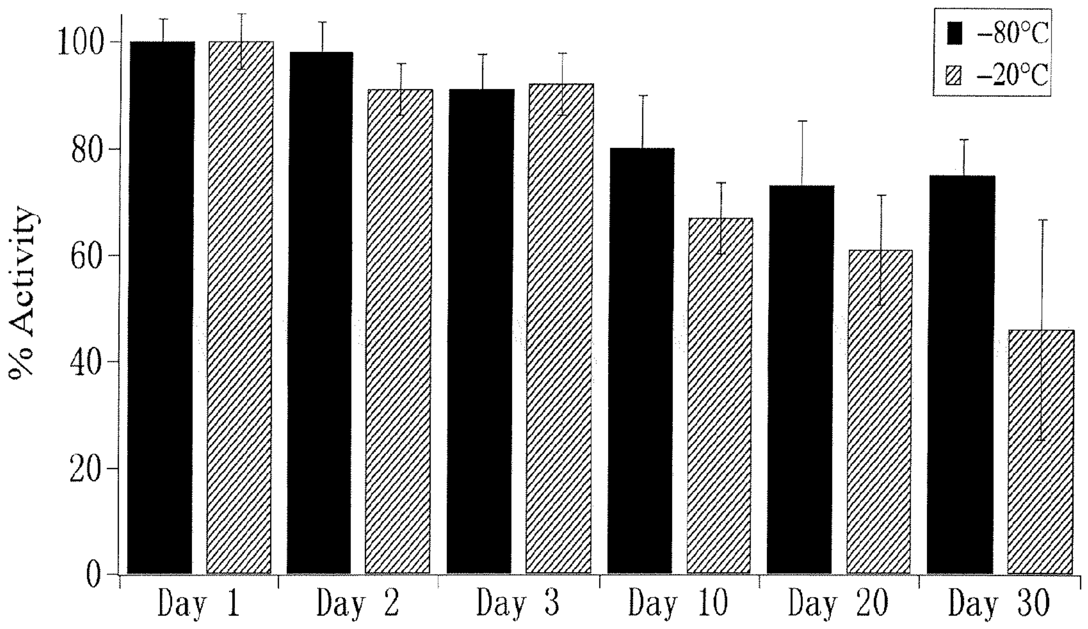
Figure 6A:
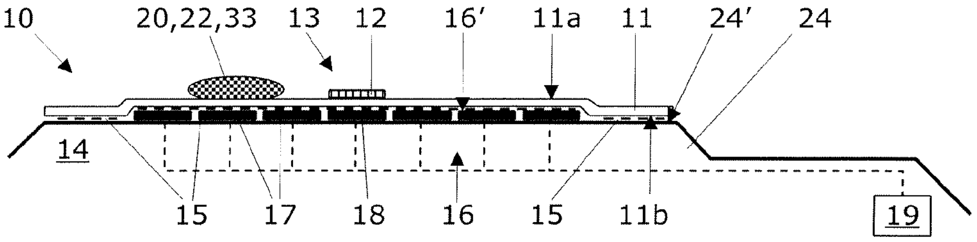
Figure 6B:
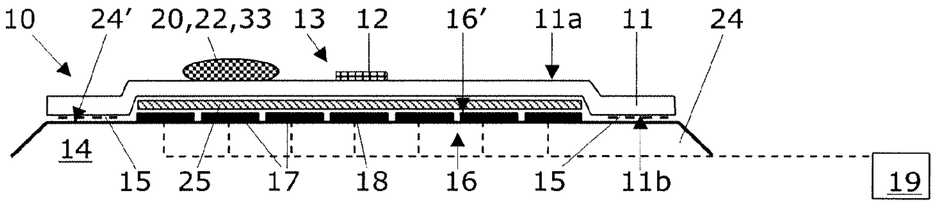
Figure 6C:
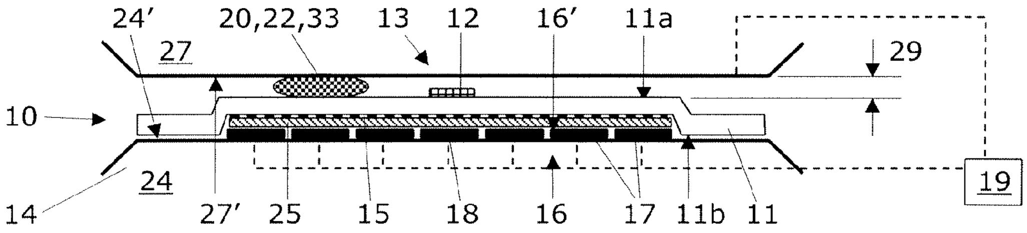
Figure 6D:
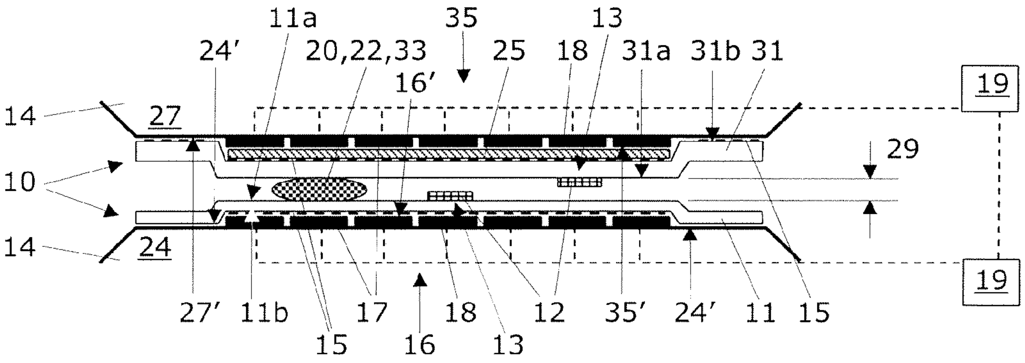

(1) a fresh piece of a carrier in the form of a plastic sheet with a dry reagent is affixed to a DMF device;

(2) reagents in droplets are actuated over on top of the carrier, exposed to the preloaded dry reagent, merged, mixed and incubated to result in a chemical reaction product;

(3) residue is left behind as a consequence of non-specific adsorption of analytes;

(4) the carrier with a product droplet or dried product is peeled off; and (5) the product is analyzed if desired;

FIG. 3 MALDI-MS analysis of different analytes processed on different carriers using a single DMF device:

a) 35 μM Insulin b) 10 μM Bradykinin c) 10 μM 20 mer DNA Oligonucleotide d) 0.01% ultramarker;

FIG. 4 pre-loaded carrier analysis. MALDI peptide mass spectra from pre-spotted (Top) trypsin and (Bottom) α-chymotrypsin digest of ubiquitin were shown, peptide peaks were identified through database search in MASCOT, and the sequence coverage was calculated to be over 50%;

FIG. 5 a bar graph showing percent activity versus time showing the pre-loaded carrier stability assay in which the fluorescence of protease substrate (BODIPY-casein) and an internal standard were evaluated after storing carriers for 1, 2, 3, 10, 20, and 30 days, the carriers were stored at −20° C. or −80° C. as indicated on the bar graph, and the mean response and standard deviations were calculated for each condition from 5 replicate carriers;

FIG. 6 different embodiments of DMF devices according to the present invention, wherein:

FIG. 6A shows a one-sided open DMF device with one carrier pre-loaded with reagents attached to a first substrate;

FIG. 6B shows a one-sided open DMF device with one carrier pre-loaded with reagents and a dielectric layer below the carrier;

FIG. 6C shows a one-sided closed DMF device with a second substrate defining a space or gap between the first and second substrates;

FIG. 6D shows a two-sided closed DMF device with a second substrate defining a space or gap between the first and second substrates.

DETAILED DESCRIPTION OF THE INVENTION

Generally speaking, the systems described herein are directed to exchangeable, reagent pre-loaded carriers for digital microfluidic devices, particularly suitable for high throughput assay procedures. As required, embodiments of the present invention are disclosed herein. However, the disclosed embodiments are merely exemplary, and it should be understood that the invention may be embodied in many various and alternative forms. The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to exchangeable, reagent pre-loaded carriers for digital microfluidic devices.

As used herein, the term "about", when used in conjunction with ranges of dimensions of particles or other physical or chemical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

The basic problem to be solved by the present invention is to provide a means of adapting digital microfluidic devices so that they can be used for high throughput batch processing while at the same time avoiding bio-fouling of the DMF devices as discussed above in the Background. To illustrate how problematic bio-fouling is, studies have been carried out by the inventors to ascertain the scope of this problem.

Protein Adsorption on DMF and Cross Contamination Analysis

Confocal microscopy was used to evaluate protein adsorption on surfaces. In general, a droplet containing 7 μg/ml FITC-BSA is translated on a DMF device. Two images were taken on a spot before and after droplet actuation. A residue is left on the surface as a consequence of non-specific protein adsorption during droplet actuation in which it can be detected by confocal microscopy. Such residues can cause two types of problems for DMF:

(1) the surface may become sticky, which impedes droplet movement, and (2) if multiple experiments are to be performed, cross-contamination may be a problem.

Figure 1A:
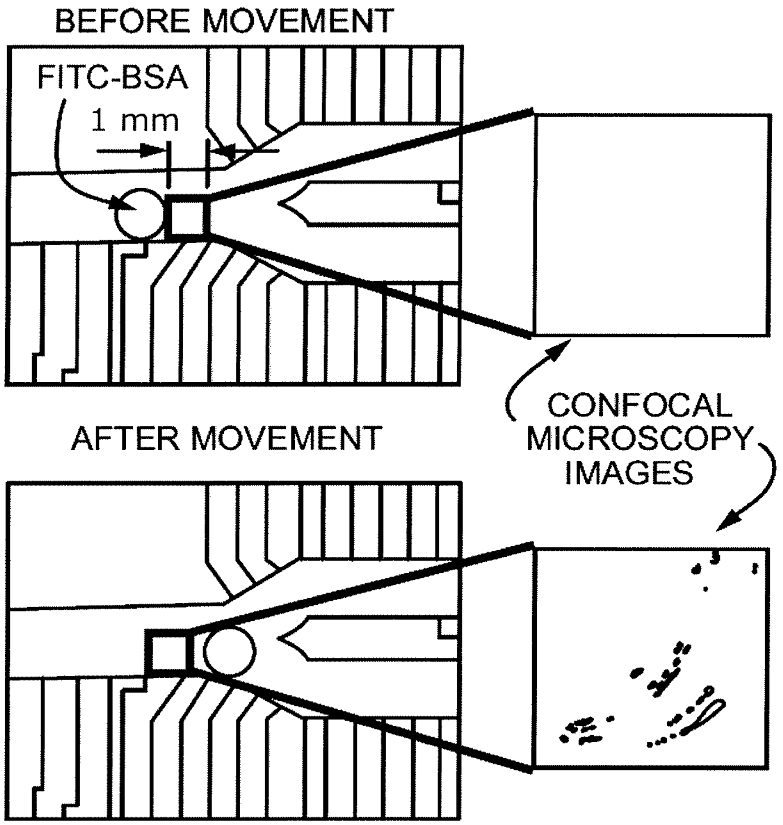
FIG. 1A protein adsorption from an aqueous droplet onto a DMF device in which the upper image shows a device prior to droplet actuation, paired with a corresponding confocal image of a central electrode, the lower image shows the same device after a droplet containing FITC-BSA (7 μg/ml) has been cycled over the electrode 4 times, paired with a confocal image collected after droplet movement. The two images were processed identically to illustrate that confocal microscopy can be used to detect the non-specific protein adsorption on device surfaces as a result of digital actuation.

A FluoView 300 scanning confocal microscope (OLYMPUS, Markam, ON) equipped with an $Ar^+$ (488 nm) laser was used, in conjunction with a 100× objective (N.A. 0.95) for analysis of proteins adsorbed to DMF device surfaces (FIG. 1A). Fluorescence from adsorbed labeled proteins was passed through a 510-525 nm band-pass filter, and each digital image was formed from the average of four frames using FluoView image acquisition software (OLYMPUS).

Figure 1B:
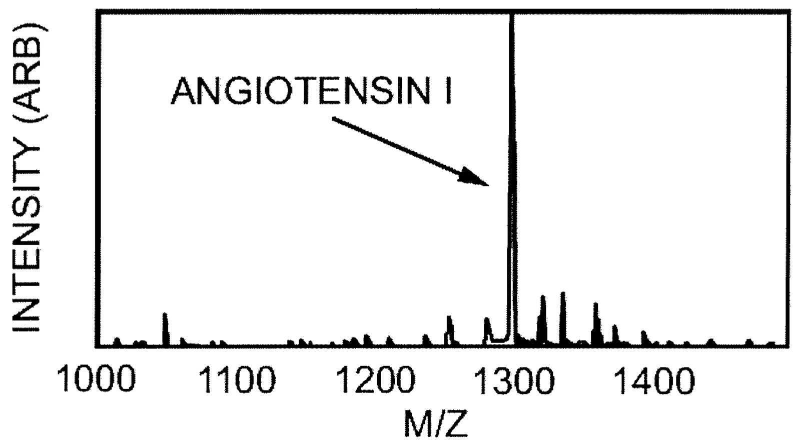
FIG. 1B mass spectrum of 10 μM angiotensin I (MW 1296)
Figure 1C:
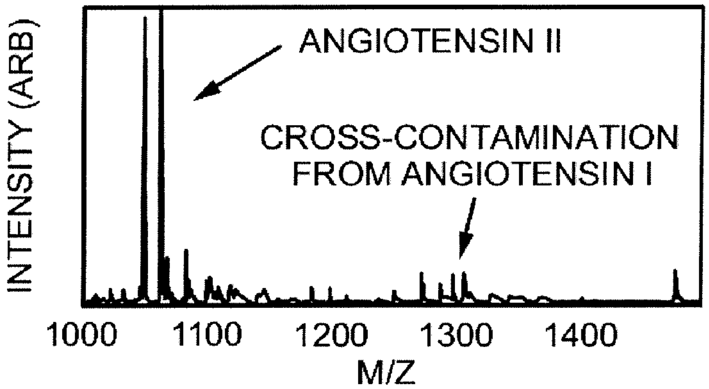
FIG. 1C cross-contamination on a digital microfluidic device: mass spectrum of 1 μM angiotensin II (MW 1046). The droplet was actuated over the same surface as the former on the same device, resulting in cross-contamination from angiotensin I.

MALDI-MS was used to evaluate the amount of cross contamination of two different peptide samples actuated across the same path on the same device. Specifically, 2 μl droplet of 10 μM angiotensin I in the first run, and 2 μl droplet of 1 μM angiotensin II in the second. As shown in FIG. 1B, the spectrum of angiotensin I generated after the first run is relatively clean; however, as shown in FIG. 1C, the spectrum of angiotensin II generated is contaminated with residue from the previous run. In these tests, after actuation by DMF, the sample droplets were transferred to a MALDI target for crystallization and analysis, meaning that the cross-contamination comprised both (a) an adsorption step in the first run, and (b) a desorption step in the second run. The intensity from the Angiotensin I contaminant was estimated to be around 10% of most intense Angiotensin II peak (MW 1046). This corresponds to roughly about 1% or 0.1 μM of Angiotensin I fouling non-specifically on the DMF device. Even though the tested peptides are less sticky compare to proteins, this result is in agreement with Luk's reported value, which is less than 8% of FITC-BSA adsorbing to DMF device (see Luk et al. 2008 "Pluronic additives: A solution to sticky problems in digital microfluidics," *Langmuir* 24: 6382-6389). In addition to contamination, smooth droplet movement, especially during the run of angiotensin II sample, was obstructed due to non-specific adsorption of previous run. Thus, a higher actuation voltage was required to force the droplet to move over to the next set of electrodes. This however does not always work if the droplet becomes stuck permanently due to high adhesion to the fouled surfaces, increasing actuation voltage will not help in this case, not to mention potential dielectric breakdown and ruin the device if the voltage is too high.

Exchangeable, Pre-Loaded, Disposable Carriers

The present invention provides exchangeable, pre-loaded, disposable carriers on which reagents are strategically located in pre-selected positions on the upper surface. These carriers can be used as exchangeable carriers for use with digital microfluidic devices where the carrier is applied to the electrode array of the digital microfluidic device.

Figure 2:
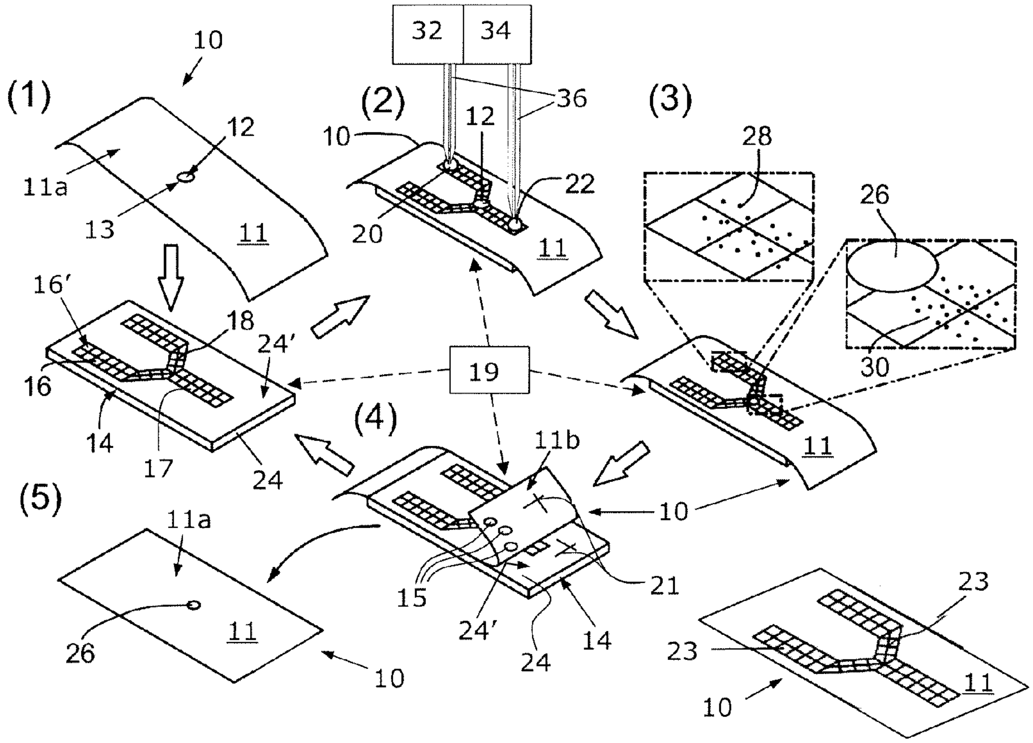
FIG. 2 a schematic depicting the removable pre-loaded carrier strategy where in step.

Referring to FIG. 2, a pre-loaded, electrically insulating disposable sheet shown generally at 10 according to the present invention has one pre-loaded reagent depot 12 mounted on a hydrophobic front surface of electrically insulating sheet 10. This disposable carrier 10 may be any thin dielectric sheet or film so long as it is chemically stable toward the reagents pre-loaded thereon. For example, any polymer based plastic may be used, such as for example saran wrap. In addition to plastic food-wrap, other carriers, including generic/clerical adhesive tapes and stretched sheets of paraffin, were also evaluated for use as replaceable DMF carriers.

The disposable carrier 10 is affixed to the electrode array 16 of the DMF device 14 with a back surface of the carrier 10 adhered to the electrode array 16 in which the reagent depot 12 deposited on the surface of the carrier 10 (across which the reagent droplets are translated) is aligned with pre-selected individual electrode 18 of the electrode array 16 as shown in steps (1) and (2) of FIG. 2. Two reagents droplets 20 and 22 are deposited onto the device prior to an assay. This depositing of the droplets 20 and 22 is preferably done utilizing dispenser tips 36 that are connected to a sample reservoir 32 or to solvent reservoir 34 (see FIG. 2). Alternatively, reservoirs 32 and 34 can be in connections with a device or are integral parts of a device whereby droplet 20 and 22 are dispensed from the reservoirs using DMF actuation.

As can be seen from step (3) of FIG. 2, during the assay reagent droplets 20 and 22 are actuated over the top of disposable sheet or carrier 10 to facilitate mixing and merging of the assay reagent droplets 20 and 22 with the desired reagent depot 12 over electrode 18. After the reaction has been completed, the disposable carrier 10 may then be peeled off as shown in step (4) and the resultant reaction products 26 analyzed if desired as shown in step (5). A fresh disposable carrier 10 is then attached to the DMF device 14 for next round of analysis. The product 26 can be also analyzed while the removable carrier is still attached to the DMF device 14. This process can be recycled by using additional pre-loaded carriers. In addition, the droplets containing reaction product(s) may be split, mixed with additional droplets, and/or incubated for cell culture if they contain cells.

As a consequence, cross contamination is avoided as residues 28 and 30 from assays conducted on a previous disposable sheet or carrier 10 will be removed along with the disposable carrier 10. The assay described above was done using one preloaded reagent 12 but it will be appreciated that the pre-loaded carrier 10 can be loaded with multiple reagents assayed in series or in parallel with multiple droplet reagents 20 and 22.

In an embodiment of the present invention the pre-loaded electrically insulating sheet 11 and the electrode array 16 may each include alignment marks for aligning the electrically insulating sheet 11 with the electrode array when affixing the electrically insulating sheet to the electrode array such that one or more pre-selected positions 13 on front working surface 11*a* of the electrically insulating sheet 11 are selected to be in registration with one or more pre-selected discrete actuating electrodes 18 of the electrode array. When the reagent depots 12 are in registration with pre-selected electrodes 18 they may be located over top of a selected electrode or next to it laterally so that it is above a gap between adjacent electrodes.

FIG. 6A shows a one-sided open DMF device with a carrier 10 that is pre-loaded with reagents 12 for use with a digital microfluidic device 14 and that is attached to a first substrate 24. The digital microfluidic device includes an array 16 of discrete electrodes 17 and an electrode controller 19. The pre-loaded carrier 10 comprises an electrically insulating sheet 11 having a front hydrophobic surface 11*a* and a back surface 11*b*. This electrically insulating sheet 11 is removably attachable to a surface 16' of the electrode array 16 of the digital microfluidic device 14. When positioned on the electrode array 16 of the digital microfluidic device 14, said electrically insulating sheet 11 covers said discrete electrodes 17 and provides electrical insulation to the discrete electrodes 17 from each other and from liquid droplets 20,22,33 present on the front hydrophobic surface 11*a*. The electrically insulating sheet 11 according to a first embodiment of the present invention has one or more reagent depots 12 located in one or more pre-selected positions 13 on its front hydrophobic surface 11*a*. In operation, the electrode controller 19 of the digital microfluidic device 14 is capable of selectively actuating and de-actuating said discrete electrodes 17 for translating liquid droplets 20,22,33 over the front hydrophobic surface 11*a* of the electrically insulating sheet 11 and said one or more pre-selected positions 13 on the front working surface 11*a* of said electrically insulating sheet 11 are positioned to be accessible to droplets 20,22,33 actuated over the front hydrophobic surface 11*a* of the electrically insulating sheet 11.

Preferably, said electrically insulating sheet 11 is attachable or attached to the surface 16' of said electrode array 16 by an adhesive 15 that contacts the back surface 11*b* of the electrically insulating sheet 11 with the surface 16' of the electrode array 16 and/or the surface 24' of the first substrate 24. It is even more preferred that said electrically insulating sheet 11 includes an adhesive 15 on said back surface 11*b* thereof which is able to contact said electrode array for adhering said electrically insulating sheet to said first substrate 24.

FIG. 6B shows a one-sided open DMF device with one carrier pre-loaded with reagents and a dielectric layer below the carrier. The digital microfluidic device 14 (as depicted similarly in FIG. 6A) includes important features such as an electrode controller 19; in addition, liquid droplets 20,22,33 to be translated are presented here. However, in the embodiment as shown in FIG. 6B, the adhesive 15 only contacts the back surface 11*b* of the electrically insulating sheet 11 with the surface 24' of the first substrate 24; alternately, the adhesive 15 could be present on the entire back surface 11*b* of the electrically insulating sheet 11 (not shown). In this embodiment, the digital microfluidic device 14 preferably includes a dielectric layer 25 applied directly to said surface 16' of said electrode array 16 so that it is sandwiched between said electrode array 16 and said electrically insulating sheet 11.

FIG. 6C shows a one-sided closed DMF device with a second substrate defining a space or gap between the first and second substrates. The digital microfluidic device 14 (as depicted similarly in FIG. 6B) includes important features such as an electrode controller 19; in addition, liquid droplets 20,22,33 to be translated are present. In this embodiment, the digital microfluidic device 14 preferably further includes a second substrate 27 having a front surface 27' which is optionally a hydrophobic surface. The second substrate 27 is in a spaced relationship to the first substrate 24 thus defining a space or gap 29 between the first and second substrates 24,27 capable of containing droplets 20,22,33 between the front surface 27' of the second substrate 27 and the front hydrophobic surface 11*a* of the electrically insulating sheet 11 on said electrode array 16 on said first substrate 24. Preferably, the electrode controller 19 also controls an electrostatic charge of the second substrate surface 27'. In contrast to FIG. 6B, the adhesive 15 here only contacts the back surface 11*b* of the electrically insulating sheet 11 with the dielectric layer 25 that is positioned on the surface 16' of the electrode array 16 of the first substrate 24. Alternately, the adhesive 15 could be present on the entire back surface 11*b* of the electrically insulating sheet 11 (not shown).

FIG. 6D shows a two-sided closed DMF device with a second substrate defining a space or gap between the first and second substrates. The digital microfluidic device 14 (as depicted similarly in the FIGS. 6A-6C) includes an array 16 of discrete electrodes 17 and an electrode controller 19. The pre-loaded carrier 10 comprises a first electrically insulating sheet 11 having a front hydrophobic surface 11*a* and a back surface 11*b*. This first electrically insulating sheet 11 is removably attachable to a surface 16' of a first electrode array 16 of the digital microfluidic device 14. In this embodiment, the digital microfluidic device 14 preferably further includes a second substrate 27 having a front surface 27'. The front surface 27' of the second substrate 27 according to a preferred embodiment is not hydrophobic and it includes an additional, second electrically insulating sheet 31 having a back surface 31*b* and a front hydrophobic surface 31*a*. This additional electrically insulating sheet 31 is removably attached to said front surface 27' of the second substrate 27 with the back surface 31*b* adhered to said front surface 27'. Said additional electrically insulating sheet 31 has none, one or more reagent depots 12 located in one or more pre-selected positions 13 on the front hydrophobic surface 31*a* of the additional electrically insulating sheet 31.

In contrast to FIG. 6B, the adhesive 15 here only contacts the back surface 11*b* of the electrically insulating sheet 11 with the surface 16' of the electrode array 16 of the first substrate 24. On the opposite side, the adhesive 15 is present on the entire back surface 31*b* of the additional electrically insulating sheet 31. Alternately, the adhesive 15 could be present on the entire back surface 11*b* of the electrically insulating sheet 11 (not shown). Preferably (as shown in FIG. 6D), the digital microfluidic device 14 includes an additional electrode array 35 mounted on the front surface 27' of the second substrate 27, the additional electrode array 35 being covered by the additional electrically insulating sheet 31 having said front hydrophobic surface 31*a*. As shown in FIGS. 6B and 6C, also this digital microfluidic device 14 of FIG. 6D preferably includes a dielectric layer 25 applied directly to said surface 27' of said second electrode array 35 so that it is sandwiched between said electrode array 35 and said second electrically insulating sheet 31. Another dielectric layer 25 may be positioned between the electrically insulating sheet 11 and the surface 16' of the electrode array 16 (not shown). In an alternate embodiment (not shown), said additional electrode array 35 on the second substrate 27 is coated with a hydrophobic coating and the second insulating layer 31 is not present.

The disposable carriers 10 may be packaged with a plurality of other carriers and sold with the reagent depots containing one or more reagents selected for specific assay types. Thus the carriers 10 in the package may have an identical number of preloaded reagent depots 12 with each depot including an identical reagent composition. The reagent depots preferably include dried reagent but they could also include a viscous gelled reagent.

One potential application of the present invention may be culturing and assaying cells on regent depots. In such applications the reagent depots can include bio-substrate with attachment factors for adherent cells, such as fibronectin, collagen, laminin, polylysine, etc. and any combination thereof. Droplets with cells can be directed to the bio-substrate depots to allow cell attachment thereto in the case of adherent cells. After attachment, cells can be cultured or analyzed in the DMF device.

While the DMF device 14 has been shown in FIG. 2 to have a single substrate 24 with an electrode array 16 formed thereon, it will be appreciated by those skilled in the art that the DMF device may include a second substrate 27 having a front surface 27' which is optionally a hydrophobic surface, wherein the second substrate is in a spaced relationship to the first substrate thus defining a space between the first and second substrates capable of containing droplets between the front surface of the second substrate and the front hydrophobic surface of the electrically insulating sheet on said electrode array on the first substrate (see FIG. 6C). The second substrate may be substantially transparent. Departing from the embodiment as depicted in FIG. 6C, the pre-loaded carrier 10 (comprising a first electrically insulating sheet 11 and having a front hydrophobic surface 11*a* and a back surface 11*b*) may be removably attached to the surface 27' of the second substrate 27 of the digital microfluidic device 14. The same time, the electrode array 16 may be coated with a non-removable electrical insulator (not shown).

When the front surface of the second substrate is not hydrophobic, the device may include an additional electrically insulating sheet having a back surface and a front hydrophobic surface being removably attachable to the front surface of the second substrate with the back surface adhered to the front surface and additional electrically insulating sheet has one or more reagent depots located in one or more pre-selected positions on the front hydrophobic surface of the electrically insulating sheet.

Additionally, there may be included an additional electrode array 35 mounted on the front surface 27' of the second substrate 27, and including a layer applied onto the additional electrode array 35 having a front hydrophobic surface. The layer applied onto the additional electrode array has a front hydrophobic surface 31*a* which may be an additional electrically insulating sheet 31 having one or more reagent depots 12 located in one or more pre-selected positions 13 on the front hydrophobic surface. In this two plate design as depicted in FIG. 6D, the first substrate 24 may optionally not have the pre-loaded insulating sheet or carrier 11 with reagent depots 12 mounted thereon.

The present invention and its efficacy for high throughput assaying will be illustrated with the following studies and examples, which are meant to be illustrative only and non-limiting.

EXPERIMENTAL DETAILS

Reagents and Materials

Working solutions of all matrixes (α-CHCA, DHB, HPA, and SA) were prepared at 10 mg/ml in 50% analytical grade acetonitrile/deionized (DI) water (v/v) and 0.1% TFA (v/v) and were stored at 4° C. away from light. Stock solutions (10 μM) of angiotensin I, II and bradykinin were prepared in DI water, while stock solutions (100 μM) of ubiquitin and myoglobin were prepared in working buffer (10 mM Tris-HCl, 1 mM $CaCl_2$ 0.0005% w/v Pluronic F68, pH 8). All stock solutions of standards were stored at 4° C. Stock solutions (100 μM) of digestive enzymes (bovine trypsin and α-chymotrypsin) were prepared in working buffer and were stored as aliquots at −80° C. until use. Immediately preceding assays, standards and enzymes were warmed to room temperature and diluted in DI water (peptides) and working buffer (proteins, enzymes, and fluorescent reagents). Flourescent assay solution (3.3 μM quenched, bodipy-casein and 2 μM rhodamine B in working buffer) was prepared immediately prior to use.

Device Fabrication and Operation

Digital microfluidic devices with 200 nm thick chromium electrodes patterned on glass substrates were fabricated using standard microfabrication techniques. Prior to experiments, devices were fitted with (a) un-modified carriers, or (b) reagent-loaded carriers. When using un-modified carriers (a), a few drops of silicone oil were dispensed onto the electrode array, followed by the plastic covering. The surface was then spin-coated with Teflon-AF (1% w/w in Fluorinert FC-40, 1000 RPM, 60 s) and annealed on a hot plate (75° C., 30 min). When using pre-loaded carriers (b), plastic coverings were modified prior to application to devices. Modification comprised three steps: adhesion of coverings to unpatterned glass substrates, coating with Teflon-AF (as above), and application of reagent depots. The latter step was achieved by pipetting 2 μl droplet(s) of enzyme (6.5 μM trypsin or 10 μM α-chymotrypsin) onto the surface, and allowing it to dry. The pre-loaded carrier was either used immediately, or sealed in a sterilized plastic Petri-dish and stored at −20° C. Prior to use, pre-loaded carriers were allowed to warm to room temperature (if necessary), peeled off of the unpatterned substrate, and applied to a silicone-oil coated electrode array, and annealed on a hot plate (75° C., 2 min). In addition to food wraps, plastic tapes and paraffin have also been used to fit onto the device. Tapes were attached to the device by gentle finger press, whereas paraffin are stretched to about 10 mm thickness and then wrap around the device to make a tight seal free of air bubbles.

Devices had a "Y" shape design of 1 mm×1 mm electrodes with inter-electrode gaps of 10 μm. 2 μl droplets were moved and merged on devices operating in open-plate mode (i.e., with no top cover) by applying driving potentials (400-500 $V_{RMS}$) to sequential pairs of electrodes. The driving potentials were generated by amplifying the output of a function generator operating at 18 kHz, and were applied manually to exposed contact pads. Droplet actuation was monitored and recorded by a CCD camera.

Analysis by MALDI-MS

Matrix assisted laser desorption/ionization mass spectrometry (MALDI-MS) was used to evaluate samples actuated on DMF devices. Matrix/sample spots were prepared in two modes: conventional and in situ. In conventional mode, samples were manipulated on a device, collected with a pipette and dispensed onto a stainless steel target. A matrix solution was added, and the combined droplet was allowed to dry. In in situ mode, separate droplets containing sample and matrix were moved, merged, and actively mixed by DMF, and then allowed to dry onto the surface. In in situ experiments involving pre-loaded carriers, matrix/crystallization was preceded by an on-chip reaction: droplets containing sample proteins were driven to dried spots containing digestive enzyme (trypsin or α-chymotrypsin). After incubation with the enzyme (room temp., 15 min), a droplet of matrix was driven to the spot to quench the reaction and the combined droplet was allowed to dry. After co-crystallization, carriers were carefully peeled off of the device, and then affixed onto a stainless steel target using double-sided tape. Different matrixes were used for different analytes: α-CHCA for peptide standards and digests, DHB for ultramarker, HPA for oligonucleotides and SA for proteins. At least three replicate spots were evaluated for each sample.

Samples were analyzed using a MALDI-TOF Micro-MX MS (Waters, Milford, Mass.) operating in positive mode. Peptide standards and digests were evaluated in reflectron mode over a mass to charge ratio (m/z) range from 500-2'000. Proteins were evaluated in linear mode over a m/z range from 5'000-30'000. At least one hundred shots were collected per spectrum, with laser power tuned to optimize the signal to noise ratio (S/N). Data were then processed by normalization to the largest analyte peak, baseline subtraction, and smoothed with a 15-point running average. Spectra of enzyme digests were analyzed with the Mascot protein identification package searching the SwissProt database. The database was searched with 1 allowed missed cleavage, a mass accuracy of +/−1.2 Da, and no further modifications.

Peptide/Protein MS Analysis on Exchangeable Carriers

To illustrate the new strategy, four different types of analytes were processed using a single DMF device, using afresh removable carrier for each run. As shown in FIG. 3, the four analytes included insulin (MW 5733), bradykinin (MW 1060), a 20-mer oligonucleotide (MW 6135), and the synthetic polymer, Ultramark 1621 (MW 900-2200). Each removable carrier was analyzed by MALDI-MS in-situ, and no evidence for cross-contamination was observed. In our lab, conventional devices are typically disposable (used once and then discarded); however, in experiments with removable carriers, we regularly used devices for 9-10 assays with no drop-off in performance. Thus, in addition to eliminating cross-contamination, the removable carrier strategy significantly reduces the fabrication load required to support DMF.

In addition to plastic food-wrap, other carriers, including clerical adhesive tape and stretched sheets of wax film, were also evaluated for use as replaceable carriers. As was the case for food wrap, carriers formed from tape and wax film were found to support droplet movement and facilitate device re-use (data not shown). In addition, carriers formed from these materials were advantageous in that they did not require an annealing step prior to use. Other concerns, however, made these materials less attractive. Coverings formed from adhesive tape tended to damage the actuation electrodes after repeated applications (although presumably, this would not be a problem for low-tack tapes). In addition, as the tape carriers tested were relatively thick (~45 μm), larger driving potentials (~900 $V_{RMS}$) were required for droplet manipulation. In contrast, the thickness of stretched wax was ~10 μm, resulting in driving potentials similar to those used for carriers formed from food wrap. However, the thickness of carriers formed in this manner was observed to be non-uniform, making them less reliable for droplet movement. In summary, it is likely that a variety of different carriers are compatible with the removable covering concept, but because those formed from food-wrap performed best in our hands, we used this material for the experiments reported here.

Two drawbacks to the removable carrier strategy are trapped bubbles and material incompatibility. In initial experiments, bubbles were occasionally observed to become trapped between the carrier and the device surface during application. When a driving potential was applied to an electrode near a trapped bubble, arcing was observed, which damaged the device. We found that this problem could be overcome by moistening the device surface with a few drops of silicone oil prior to application of the plastic film. Upon annealing, the oil evaporates, leaving a bubble-free seal. The latter problem, material incompatibility, is more of a concern. If aggressive solvents are used, materials in the carrier might leach into solution, which could interfere with assays. In our experiments, no contaminant peaks were observed in any MALDI-MS spectra (including in control spectra generated from bare carrier surfaces, not shown), but we cannot rule out the possibility of this being a problem in other settings. Given the apparent wide range of materials that can be used to form carriers (see above), we are confident that alternatives could be used in cases in which Teflon-coated food wrap is not tenable.

Preloaded Carriers and its Stability Analysis

In exploring exchangeable carrier strategy to overcome fouling and cross-contamination, we realized that the technology could, in addition, serve as the basis for an exciting new innovation for digital microfluidics. By pre-depositing reagents onto carriers (and by having several such carriers available), this strategy transformed DMF techniques into a convenient new platform for rapid introduction of reagents to a device, and can be a solution to the well-known world-to-chip interface problem for microfluidics (see Fang et al. 2002 "A high-throughput continuous sample introduction interface for microfluidic chip-based capillary electrophoresis systems" *Analytical Chemistry* 74: 1223-1231 and Liu et al. 2003 "Solving the "World-to-chip" Interface problem with a microfluidic matrix" *Analytical Chemistry* 75: 4718-4723).

To illustrate the new strategy, we prepared food wraps pre-spotted with dry digestive enzymes, and then used DMF to deliver droplets containing the model substrate, ubiquitin, to the spots. After a suitable incubation period, droplets containing MALDI matrix were delivered to the spot, which was dried and then analyzed. As shown in FIG. 4, MALDI mass spectra were consistent with what is expected of peptide mass fingerprints for the analyte. In fact, when evaluated using the proteomic search engine, MASCOT, the performance was excellent, with sequence identification of 50% or above for all trials.

In optimizing the pre-loaded carrier strategy for protease assays, we observed the method to be quite robust. First, pluronic F68 was used as a solution additive to facilitate movement of the analyte droplet (in this case, ubiquitin); this reagent has been shown to reduce ionization efficiencies for MALDI-MS (see Boernsen et al. 1997 "Influence of solvents and detergents on matrix-assisted laser desorption/ionization mass spectrometry measurements of proteins and oligonucleotides" *Rapid Communications in Mass Spectrometry* 11: 603-609). Fortunately, the amount used here (0.0005% w/v) was low enough such that this effect was not observed. Second, trypsin and α-chymotrypsin autolysis peaks were only rarely observed, which we attribute to the low enzyme-to-substrate ratio and the short reaction time. Third, in preliminary tests, we determined that the annealing step (75° C., 2 min) did not affect the activity of dried enzymes. In the future, if reagents sensitive to these conditions are used, we plan to evaluate carriers formed from materials that do not require annealing (such as low-tack tape). Regardless, the robust performance of these first assays suggests that the strategy may eventually be useful for a wide range of applications, such as immunoassays or microarray analysis.

As described, the preloaded carrier strategy is similar to the concept of pre-loaded reagents stored in microchannels (see Linder et al. 2005; Hatakeyama et al. 2006; Zheng et al. 2005; Furuberg et al. 2007; Garcia et al. 2004; Zimmermann et al. 2008; and Chen et al. 2006 "Microfluidic cartridges preloaded with nanoliter plugs of reagents: An alternative to 96-well plates for screening" *Current Opinion in Chemical Biology* 10: 226-231). Unlike these previous methods, in which devices are typically disposed of after use, in the present preloaded carrier strategy, the fundamental device architecture can be reused for any number of assays. Additionally, because the reagents (and the resulting products) are not enclosed in channels, they are in an intrinsically convenient format for analysis. For example, in this work, the format was convenient for MALDI-MS detection, but we speculate that a wide range of detectors could be employed in the future, such as optical readers or acoustic sensors. Finally, although this proof-of-principle work made use of food wrap carrier carrying a single reagent spot, we speculate that in the future, a microarray spotter could be used to fabricate preloaded carriers carrying many different reagents for multiplexed analysis.

To be useful for practical applications, pre-loaded carriers must be able to retain their activity during storage. To evaluate the shelf-life of these reagent spots, we implemented a quantitative protein digest assay. The reporter in this assay, quenched bodipy-labeled casein, has low fluorescence when intact, but becomes highly fluorescent when digested. In this preloaded reagent stability assays, a droplet containing the reporter was driven to a pre-loaded spot of trypsin, and after incubation the fluorescent signal in the droplet was measured in a plate reader (as described previously, see Luk et al. 2008 "Pluronic additives: A solution to sticky problems in digital microfluidics," *Langmuir* 24: 6382-6389; Barbulovic-Nad et al. 2008 "Digital microfluidics for cell-based assays" *Lab on a Chip* 8: 519-526; Miller and Wheeler 2008 "A digital microfluidic approach to homogeneous enzyme assays" *Analytical Chemistry* 80: 1614-1619). In preliminary experiments with freshly prepared preloaded carriers, it was determined that at the concentrations used, the reaction was complete within 30 minutes. An internal standard (IS), rhodamine B, was used to correct for alignment errors, evaporation effects, and instrument drift over time.

In shelf-life experiments, preloaded carriers were stored for different periods of time (1, 2, 3, 10, 20, or 30 days) at −20° C. or −80° C. In each experiment, after thawing the carrier, positioning it on the device, driving the droplet to the trypsin, and incubating for 30 minutes, the reporter/IS signal ratio was recorded. At least five different carriers were evaluated for each condition. As shown in FIG. 5, shelf-life performance was excellent—carriers stored at −80° C. retained >75% of the original activity for periods as long as 30 days. Carriers stored at −20° C. retained >50% of the original activity over the same period. The difference might simply be the result of different average storage temperature, or might reflect the fact that the −20° C. freezer was used in auto-defrost mode (with regular temperature fluctuations), while the temperature in the −80° C. freezer was constant. Regardless, the performance of these carriers was excellent for a first test, and we anticipate that the shelf-life might be extended in the future by adjusting the enzyme suspension buffer pH or ionic strength or by adding stabilizers such as such as trehalose, a disaccharide that have been used widely in the industry to preserve proteins in the dry state (see Draber et al. 1995 “Stability of monoclonaligm antibodies freeze-dried in the presence of trehalose” *Journal of Immunological Methods* 181: 37-43).

In summary, the inventors have developed a new strategy for digital microfluidics, which facilitates virtually un-limited re-use of devices without concern for cross-contamination, as well as enabling rapid exchange of pre-loaded reagents. The present invention allows for the transformation of DMF into a versatile platform for lab-on-a-chip applications.

As used herein, the terms “comprises”, “comprising”, “including” and “includes” are to be construed as being inclusive and open ended, and not exclusive. Specifically, when used in this specification including claims, the terms “comprises”, “comprising”, “including” and “includes” and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

The same reference numbers relate to the same features, even when these reference numbers are only displayed in the Figures and not particularly referred to in the specification.

REFERENCE NUMBERS

10 Disposable, preloaded carrier
11 Electrically insulating sheet
11*a* Front hydrophobic surface of 11; front working surface
11*b* Back surface of 11
12 Pre-loaded reagent depot
13 Pre-selected position
14 Digital microfluidic (DMF) device
15 Adhesive
16,16' Electrode array; surface of 16
17 Discrete electrodes
18 Pre-selected individual electrode
19 Electrode controller
20 Reagent droplet
21 Alignment marks
22 Reagent droplet
23 Patterned conductive coating
24,24' First substrate; surface of 24
25 Dielectric layer
26 Resultant reaction product
27,27' Second substrate; front surface of 27
28 Previous assay residue
29 Space
30 Previous assay residue
31 Additional electrically insulating sheet
31*a*,31*b* Front hydrophobic surface of 31; back surface of 31
32 Sample reservoir
33 Solvent droplet
34 Solvent reservoir
35,35' Additional electrode array; surface of 35
36 Dispenser tip

The invention claimed is:

1. An apparatus comprising components for assembling a digital microfluidic device, comprising:

a first substrate having mounted on a surface thereof a first electrode array, said first electrode array including a first array of discrete electrodes, a dielectric layer coating said first electrode array, said dielectric layer having a hydrophobic front surface;

a second substrate having a front surface; and a pre-loaded electrically insulating sheet having a back surface and a front hydrophobic surface, said pre-loaded electrically insulating sheet being removably attachable to said front surface of said second substrate, said pre-loaded electrically insulating sheet having one or more reagent depots located in one or more pre-selected positions on the front hydrophobic surface thereof;

wherein said pre-loaded electrically insulating sheet is detached from said first substrate and said second substrate;

wherein said first electrode array is connectable to an electrode controller capable of selectively actuating and de-actuating said discrete electrodes in said first array of discrete electrodes;

wherein the device is assembled by affixing the pre-loaded electrically insulating sheet to the second substrate, and providing the second substrate, having said pre-loaded electrically insulating sheet provided thereon, in a spaced relationship relative to the first substrate, thus defining a space between the first and second substrates capable of containing liquid droplets between the hydrophobic front surface of the first substrate and the front hydrophobic surface of the pre-loaded electrically insulating sheet; and wherein the one or more reagent depots are provided such that they are in spatial registration with one or more pre-selected discrete electrodes of the first electrode array upon assembly of the device.

2. The apparatus according to claim 1 wherein the second substrate comprises a second electrode array.

3. The apparatus according to claim 2 wherein said dielectric layer of said first substrate is a first dielectric layer, and wherein the second substrate comprises a second dielectric layer coating the second electrode array, such that the second dielectric layer is sandwiched between said second electrode array and said pre-loaded electrically insulating sheet when said device is assembled.

4. The apparatus according to claim 1, wherein the second substrate is substantially transparent.

5. The apparatus according to claim 1 wherein the pre-loaded electrically insulating sheet and the second substrate each further comprise one or more alignment marks for aligning the pre-loaded electrically insulating sheet with the first electrode array when affixing the pre-loaded electrically insulating sheet to the second substrate, such that one or more preselected positions on front hydrophobic surface of the pre-loaded electrically insulating sheet are selected to be in registration with one or more of the discrete electrodes of the first electrode array.

6. The apparatus according to claim 1 wherein the pre-loaded electrically insulating sheet includes an adhesive on the back surface thereof which is able to contact the second substrate for adhering the pre-loaded electrically insulating sheet to the second substrate.

7. The apparatus according to claim 1 wherein the one or more reagent depots are more than one reagent depot, wherein each reagent depot contains at least one reagent different from reagents in at least one of all other reagent depots.

8. The apparatus according to claim 1 wherein each reagent depot comprises a dried reagent or a viscous gelled reagent.

9. The apparatus according to claim 1 wherein one or more reagent depots include one single reagent or at least two reagents.

10. The apparatus according to claim 1 wherein one or more reagent depots includes bio-substrates for cell adhesion.

11. The apparatus according to claim 10 wherein one or more of said bio-substrates includes any one of fibronectin, collagen, laminin, polylysine, and any combination thereof.

12. The apparatus according to claim 1 further comprising one or more additional pre-loaded electrically insulating sheets.

13. The apparatus according to claim 12 wherein each pre-loaded electrically insulating sheet has an identical number of reagent depots.

14. The apparatus according to claim 1 further comprising the electrode controller.

15. The apparatus according to claim 1 wherein the pre-loaded electrically insulating sheet carries a patterned conductive coating that can be used to provide a reference or actuating potential to the first electrode array.

16. An apparatus comprising components for assembling a digital microfluidic device, comprising:

a first substrate having mounted on a surface thereof a first electrode array, said first electrode array including a first array of discrete electrodes, said first substrate having a front surface;

an optional second substrate having a front surface; and a pre-loaded electrically insulating sheet having a back surface and a front hydrophobic surface, said pre-loaded electrically insulating sheet being removably attachable to said front surface of said first substrate, said pre-loaded electrically insulating sheet having one or more reagent depots located in one or more pre-selected positions on the front hydrophobic surface thereof;

wherein said pre-loaded electrically insulating sheet is detached from said first substrate and said optionally provided second substrate;

wherein said first electrode array is connectable to an electrode controller capable of selectively actuating and deactuating said discrete electrodes in said first array of discrete electrodes;

wherein the device is assembled by affixing the pre-loaded electrically insulating sheet to the first substrate, and optionally, providing the second substrate in a spaced relationship relative to the first substrate, thus optionally defining a space between the first and second substrates capable of containing liquid droplets between the hydrophobic front surface of the first substrate and the front hydrophobic surface of the pre-loaded electrically insulating sheet; and wherein the one or more reagent depots are provided such that they are in spatial registration with one or more pre-selected discrete electrodes of the first electrode array upon assembly of the device.

17. The apparatus according to claim 16 wherein the first substrate comprises a first dielectric layer coating the first electrode array, such that the first dielectric layer is sandwiched between the first electrode array and the pre-loaded electrically insulating sheet when the device is assembled.

18. The apparatus according to claim 16 wherein the pre-loaded electrically insulating sheet and the first substrate each further comprise one or more alignment marks for aligning the pre-loaded electrically insulating sheet the first electrode array when affixing the pre-loaded electrically insulating sheet to the first substrate, such that one or more preselected positions on front hydrophobic surface of the pre-loaded electrically insulating sheet are selected to be in registration with one or more of the discrete electrodes of the first electrode array.

19. The apparatus according to claim 16 wherein the pre-loaded electrically insulating sheet includes an adhesive on the back surface thereof which is able to contact the first substrate for adhering the pre-loaded electrically insulating sheet to the first substrate.

20. The apparatus according to claim 16 wherein the one or more reagent depots are more than one reagent depot, wherein each reagent depot contains at least one reagent different from reagents in at least one of all other reagent depots.

21. The apparatus according to claim 16 wherein each reagent depot comprises a dried reagent or a viscous gelled reagent.

22. The apparatus according to claim 16 wherein one or more reagent depots include one single reagent or at least two reagents.

23. The apparatus according to claim 16 wherein one or more reagent depots includes bio-substrates for cell adhesion.

24. The apparatus according to claim 23 wherein one or more of said bio-substrates includes any one of fibronectin, collagen, laminin, polylysine, and any combination thereof.

25. The apparatus according to claim 16 further comprising one or more additional pre-loaded electrically insulating sheets.

26. The apparatus according to claim 25 wherein each pre-loaded electrically insulating sheet has an identical number of reagent depots.

27. The apparatus according to claim 16 further comprising the electrode controller.

28. The apparatus according to claim 16 comprising the second substrate, and wherein the front surface of the second substrate is hydrophobic.

29. The apparatus according to claim 28 wherein the second substrate comprises a second electrode array.

30. The apparatus according to claim 28 wherein the second substrate is substantially transparent.

31. The apparatus according to claim 16 comprising the second substrate, wherein the pre-loaded electrically insulating sheet is a first pre-loaded electrically insulating sheet, the kit further comprising a second pre-loaded electrically insulating sheet having a back surface and a front hydrophobic surface, said second pre-loaded electrically insulating sheet being removably attachable to said front surface of said second substrate.

32. The apparatus according to claim 31 wherein said reagent depots of said first pre-loaded electrically insulating sheet are first regent depots, said second pre-loaded electrically insulating sheet comprises one or more second reagent depots located in one or more pre-selected positions on the front hydrophobic surface thereof.

33. The apparatus according to claim 31 wherein the one or more second reagent depots are provided such that they are in spatial registration with one or more pre-selected discrete electrodes of the first electrode array upon assembly of the device.

34. The apparatus according to claim 31 wherein the second pre-loaded electrically insulating sheet carries a patterned conductive coating that can be used to provide a reference or actuating potential to the first electrode array.

* * * * *